United States Patent [19]
Williamson et al.

[11] Patent Number: 4,697,040
[45] Date of Patent: Sep. 29, 1987

[54] ISOMERIZATION OF VINYLIDENE OLEFINS

[75] Inventors: Roger C. Williamson, Kingwood, Tex.; James J. Harrison, Novato, Calif.

[73] Assignee: Chevron Research Company, San Francisco, Calif.

[21] Appl. No.: 1,930

[22] Filed: Jan. 8, 1987

Related U.S. Application Data

[63] Continuation-in-part of Ser. No. 833,296, Feb. 25, 1986, abandoned.

[51] Int. Cl.$^4$ ............................ C07C 5/25; C07C 5/27
[52] U.S. Cl. ...................................... 585/666; 585/671
[58] Field of Search ................... 585/666, 671, 664; 423/329, 328

[56] References Cited

U.S. PATENT DOCUMENTS 3,150,202  9/1964  Holt et al. ........................ 585/666
3,236,909  2/1966  Winnick ............................ 585/666
3,697,616  10/1972 McDonough et al. ............ 585/666
3,940,452  2/1976  Strassberger ..................... 585/671
4,576,807  3/1986  Loechelt, II ..................... 423/329
4,587,374  5/1986  Peters .............................. 585/670

Primary Examiner—Asok Pal
Attorney, Agent, or Firm—S. R. La Paglia; T. G. DeJonghe

[57] ABSTRACT

A process for isomerization of vinylidene olefins at least in part to tri-substituted ethylene compound which process comprises contacting an olefinic feedstock, containing mostly vinyl olefins and minor amounts of vinylidene olefins, with a catalyst comprising LZ-Y52 zeolite so as to isomerize the vinylidene olefins to the tri-substituted ethylene compounds without losing substantial amounts of the vinyl olefins to side products. A process is preferably applied to a feedstock such as octene-1 containing 2-ethyl-hexane-1 and the 2-ethyl-hexene-1 is isomerized to 3-methyl-heptene-2 and 3-methyl-heptene-3 while retaining all or most all of the octene-1.

4 Claims, No Drawings

ISOMERIZATION OF VINYLIDENE OLEFINS

CROSS REFERENCE TO RELATED APPLICATIONS

This application is a continuation-in-part of U.S. Ser. No. 833,296 filed Feb. 25, 1986, now abandoned.

BACKGROUND OF INVENTION

This invention relates to isomerization of 2-branched-1-olefins, present in minor amounts in mixture with vinyl olefins, using a zeolitic catalyst.

In certain reactions it is desirable to use relatively pure straight chain vinyl olefins. For example, in the formation of straight chain alcohols, it is desirable to start with straight chain vinyl olefins. The straight chain vinyl olefins may be reacted with trialkyl aluminum to form new trialkyl aluminum compounds having alkyl groups corresponding to the vinyl olefins; then the new trialkyl aluminum compounds are oxidized to aluminum alkoxides; and finally the alkoxides are hydrolyzed to form straight chain alcohols.

However, if vinylidene olefins (2-branched-1-olefins) are present in the straight chain vinyl olefin feed, non-linear chain alcohols will be formed, which is generally undesirable.

Vinylidene olefins have the structure:

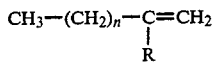

where n is zero or an integer, and R is an alkyl group.

It is desirable to convert the vinylidene olefins to tri-substituted ethylene compounds because the tri-substituted ethylene compounds interfere less with reactions, such as reactions leading to formation of linear alcohols, then do the vinylidene olefins.

Tri-substituted ethylene compounds have the formula:

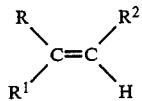

where R, $R^1$ and $R^2$ are the same or different alkyl groups.

An object of the present invention is to reduce the amount of vinylidene olefins present in a mixture containing vinyl olefins and vinylidene olefins. It is also an object of the present invention to carry out such reduction while retaining most of the vinyl olefins intact. Such reduction of vinylidene olefins is carried out using a particular isomerization process as described below.

The isomerization of olefins is known in the art. For example, Rabo, in Zeolite Chemistry and Catalysis, ACS Monogram No. 171, 1976 at page 335, discloses the isomerization of 1-butene to 2-butene using a Y zeolite catalyst. However, it is important to note that this type of isomerization would be undesirable in the present invention, at least to the extent that it reduces the amount of straight chain vinyl olefin.

U.S. Pat. No. 3,686,250 (Lanier) discloses a process for producing hydrocarbon aluminum compounds by reacting vinyl olefins with trialkyl aluminum. The Lanier patent also discloses that the vinyl olefin feedstock may be treated to reduce the content of vinylidene olefins. The treatment disclosed is selective isomerization wherein the vinylidene olefins are converted to tri-substituted olefins without significantly altering the amount of co-present vinyl olefins. Catalyst disclosed for the isomerization reaction in the Lanier patent are:

"silica gel, silicated alumina, crystalline alumino silicates (molecular sieves), activated alumina, ion exchange resins, acid clays such as montomorillonite, attapulgite, mordenite, diatomaceous earth, and so forth."

According to the Lanier patent:

"Of all the foregoing, the highly acidic materials generally have high initial reactivity; however, they are deactivated at an undesirably high rate by traces of impurities so that those materials of moderate acidity such as silica gel, activated alumina, and acidic clays are generally preferred both from a long term activity point of view and from a low cost viewpoint."

SUMMARY OF THE INVENTION

According to the present invention, a process is provided for isomerization of vinylidene olefins at least in part tri-substituted ethylene compounds, which process comprises contacting an olefinic feedstock containing mostly vinyl olefins and minor amounts of vinylidene olefins, with a catalyst comprising LZ-Y52 zeolite under olefin isomerization reaction conditions.

Preferred feedstocks for the present invention are $C_6$ to $C_{10}$ olefinic feedstocks containing at least 90 wt % vinyl olefins and containing 10 to 0.1 wt % vinylidene olefins. The preferred feedstocks include individual olefin cuts within the $C_6$ to $C_{10}$ range, such as $C_6$, $C_7$, $C_8$, $C_9$ or $C_{10}$ cuts, or mixtures of two or more of the foregoing, or the entire $C_6$ to $C_{10}$ range.

We have found that the present invention is especially advantageously applied to an octene-1 feedstock containing 2-ethyl-hexene-1. In this application the 2-ethyl-hexene-1 is isomerized, at least in part, to 3-methyl-heptene-2 and 3-methyl-heptene-3.

Thus, according to a preferred embodiment of the present invention, the feedstock to the isomerization process is at least 95 wt % octene-1 containing 5 to 0.1% 2-ethyl-hexene-1, and at least 50% of the 2-ethyl-hexene-1 is isomerized to 3-methyl-heptene-2 and 3-methyl-heptene-3 while no more than 5%, generally less than 1%, of the octene-1 is lost to side reaction products.

Among other factors, the present invention is based on my finding that in using LZ-Y52 catalyst to isomerize minor amounts of vinylidene present in a vinyl olefin feedstock, surprisingly long on-stream or run-lifes are achieved for the catalyst. Also, surprisingly low amounts of the vinyl olefin are lost due to isomerization of the vinyl olefin to other products. I have found that this is especially true when the LZ-Y52 catalyst is used to isomerize 2-ethyl-hexene-1 to 3-methyl-heptene-2 and 3-methyl-heptene-3, where the 2-ethyl-hexene-1 is present in octene-1 feedstock.

The LZ-Y52 zeolite catalyst material is commercially available from Union Carbide Corporation. LZ-Y52 is described in Sales Bulletins by Union Carbide, for example, Bulletin F-3858B, 1500, 3/78, 88-0258. The LZ-Y52 material is a synthetic crystalline aluminosilicate of a cubic arrangement having a density of 1.3 g/cc and having the following formula:

$Na_{56}[(AlO_2)_{56}(SiO_2)_{136}]\cdot 264H_2O$

LZ-Y52 can be made in, and also is commercially available in, various shapes. For example, LZ-Y52 is available as ⅛ inch or 1/16 inch extrudate pellets.

The LZ-Y52 material is a Y-type zeolite. Y-type zeolites are well known in the art, see for example, D. W. Breck, "Crystalline Molecular Sciences", J. of Chem. Ed., Vol. 41, No. 12, Dec. 1964, pp. 678-689, which disclosure is incorporated herein by reference. As noted by Breck, the composition of the Y zeolite is $Na_{56}[(AlO_2)_{56}(SiO_2)_{136}]\cdot 264H_2O$, as given above; the symmetry and cell dimension is cubic with a=24.7 Angstroms; the density is 1.3 g/cc as given above; the void volume is 0.35 cm³/g; the aperture size is 8 Angstroms and the structure is pictorially shown in FIG. 9 in the cited Breck reference. Amongst other factors, zeolite Y differs from zeolite X in that the formula for zeolite X is $Na_{56}[(AlO_2)_{86}(SiO_2)_{106}]\cdot 264H_2O$.

LZ-Y52 has been described as a Y zeolite, in particular a sodium Y zeolite, which is an excellent starting material if high ion exchange capacity is desired. LZ-Y52 can be converted to LZ-Y62 by cation exchange of ammonium for sodium, with the sodium content of LZ-Y52 reduced by 80%. The chemical and physical properties of LZ-Y52 compared to LZ-Y62 are as follows: $Na_2O$, 13 wt % vs 2.5 wt % for LZ-Y62; $(NH_4)_2O$, none vs 9.8 wt % for LZ-Y62; $Na^+$ to Al molar ratio, 0.934 vs 0.18 for LZ-Y62; $NH_4^+$ to Al ratio, none vs 0.862 for LZ-Y62; $O_2$ capacity, 33.6 wt % vs 34.0 for LZ-Y62; and cell dimension "a" of 24.68 for LZ-Y52 vs 24.73 for LZ-Y62.

The relative thermal and hydrothermal stability of LZ-Y52 compared to LZ-Y62, and also to LZ-Y72 (thermally stabilized LZ-Y62) and to LZ-Y82 (low sodium LZ-Y72) are given in Table I below.

TABLE 1

|  | RELATIVE THERMAL STABILITY* | RELATIVE HYDROTHERMAL STABILITY** |
|---|---|---|
| TYPE LZ-Y52 | 760 | 85 |
| TYPE LZ-Y62 | 680 | 16 |
| TYPE LZ-Y72 | 980 | 94 |
| TYPE LZ-Y82 | 960 | 87 |

*Relative thermal stability is here defined at $T_{(50)}$, the temperature in degrees C. at which the structure is 50% decomposed after heating at constant temperature for 16 hours.
**Relative hydrothermal stability is here defined as the % surface area retained after hydrated samples are calcined, hydrated, and recalcined at 600° C.

Suitable temperatures for use in the isomerization process of the present invention are between 10° C. and 150° C. preferably between 30° C. and 120° C. and more preferably between 50° C. and 100° C. Suitable pressures for use in the isomerization process of the present invention are between 1 and 5000 psia more preferably between 10 and 100 psia and most preferably between 15 and 45 psia.

Suitable weight hourly space velocities (WHSV) for use in the isomerization process of the present invention are between 0.1 and 100, preferably between 1 and 50, and most preferably between 2 and 20. The WHSV is computed as the weight of feed per hour to the reactor divided by the weight of catalyst in the reactor.

As stated above, the process of the present invention is applied to feedstocks containing mostly vinyl olefins, but with minor amounts of vinylidene olefins also present. The amount of vinyl olefins in the feed generally is at least 80 wt %, preferably 90 wt % and more preferably at least 95 wt %. The amount of vinylidene is generally less than 20 wt %, preferably less than 5 wt %, and more preferably less than 3 wt %, for example 1/10 to 3 wt % of vinylidene olefins.

Minor amounts of other olefins and non-olefinic materials may also be present in the basically vinyl olefin feedstock material.

A typical source of the vinyl olefin feedstock containing minor amounts of vinylidene olefins is a Zeigler ethylene growth reaction for producing higher olefins such as $C_6$–$C_{10}$ olefins.

EXAMPLE

A one-inch inside diameter pipe was filled to a depth of five inches with an inert bed of quartz (preheat section) and then with six inches of LZ-Y52 catalyst (62 g). Octene-1 containing 1.68% 2-ethyl-hexene-1 was then pumped upflow through the pipe at a rate of 124 g per hour. The results for the first 165 hours of operation are shown by the data points in Table 1. The rate was increased to 248 g per hour for the last two data points. Samples were taken with the periodicity shown in the table and analyzed by gas chromatography.

A 13-X zeolite was also evaluated in the same manner (same operating conditions as above except different catalyst) with the first sample being taken after 48 hours at 48° C. This sample contained 1.68% 2-ethyl-hexene-1 (vinylidene). Initially, the 13-X zeolite, an X-type zeolite, had provided some isomerization of the vinylidene, but after 48 hours, the catalyst run-life for this application had been exceeded.

The percent "cis-2" shown in Table 1 is the percent of cis structure 2-olefins unbranched olefins in the product. The amount of trans-2-olefins is approximately 1½ times the cis 2-olefins. The data thus shows that, using the LZ-Y52 catalyst, a high percent of the vinylidene olefins was converted to non-vinylidenes without losing much of the octene-1 to internal olefins and with a relative long catalyst run-life achieved.

TABLE II

| VINYLIDENE ISOMERIZATION OVER LZ-Y52 | | | | | |
|---|---|---|---|---|---|
| Time (h) | WHSV | g Prod/g Cat. | % Vinylidene | % Cis-2 | Temp. °C. |
| 0 | — | — | 1.68 | 0.04 | — |
| 4 | 2 | — | 0.04 | 0.10 | 48 |
| 24 | 2 | 48 | 0.04 | 0.14 | 45 |
| 32 | 2 | — | 0.04 | 0.06 | 45 |
| 48 | 2 | 96 | 0.10 | 0.04 | 32 |
| 72 | 2 | 144 | 0.20 | 0.03 | 28 |
| 165 | 2 | 330 | 0.07 | 0.04 | 42 |
|  | 4 | — | 0.24 | 0.04 | 53 |
| 200 | 4 | 450 | 0.12 | 0.07 | 69 |

What is claimed is:

1. A process for isomerization of vinylidene olefins at least in part to tri-substituted ethylene compounds, which comprises contacting an olefinic feedstock, containing mostly vinyl olefins and minor amounts of vinylidene olefins, with a catalyst comprising LZ-Y52 zeolite under olefin isomerization reaction conditions.

2. A process in accordance with claim 1 wherein the olefinic feedstock is a $C_6$ to $C_{10}$ olefinic feedstock containing at least 90 wt % vinyl olefins and containing 10 to 0.1 wt % vinylidene olefins.

3. A process in accordance with claim 1 wherein the feedstock is octene-1 containing 2-ethyl-hexene-1 and the 2-ethyl-hexene-1 is isomerized, at least in part, to 3-methyl-heptene-2 and 3-methyl-heptene-3.

4. A process in accordance with claim 3 wherein the percent by weight octene-1 in the feedstock is at least 95, the percent 2-ethyl-hexene-1 is 5 to 0.1 and at least 50 percent of the 2-ethyl-hexene-1 is isomerized to 3-methyl-heptene-2 and 3-methyl-heptene-3 while no more than 1% of the octene-1 is lost to non-octene-1 reaction products.

* * * * *